United States Patent [19]

Knifton et al.

[11] Patent Number: 5,449,838

[45] Date of Patent: * Sep. 12, 1995

[54] ISOPROPYL T-BUTYL ETHER (IPTBE) GENERATION FROM CRUDE ACETONE

[75] Inventors: John F. Knifton; Ernest L. Yeakey, both of Austin; Pei-Shing E. Dai, Port Arthur, all of Tex.

[73] Assignee: Texaco Chemical Inc., White Plains, N.Y.

[*] Notice: The portion of the term of this patent subsequent to Jul. 4, 1912 has been disclaimed.

[21] Appl. No.: 175,450

[22] Filed: Dec. 30, 1993

[51] Int. Cl.$^6$ .................... C07C 41/00; C07C 43/00
[52] U.S. Cl. .................... 568/698; 568/861; 568/881; 568/903
[58] Field of Search ............... 568/861, 903, 698, 881

[56] References Cited

U.S. PATENT DOCUMENTS

| | | | |
|---|---|---|---|
| 5,081,318 | 1/1992 | Knifton | 568/698 |
| 5,144,086 | 9/1992 | Harandi et al. | 568/698 |

*Primary Examiner*—Johann Richter
*Attorney, Agent, or Firm*—James L. Bailey; Kenneth R. Priem; Cynthia L. Hunter

[57] ABSTRACT

Disclosed is a two-step process for the generation of isopropyl t-butyl ether from a crude by-product acetone stream which comprises:

a) Hydrogenating said crude acetone over a bulk metal, nickel-rich catalyst to give an isopropanol-rich effluent;

b) subjecting said isopropanol-rich intermediate to etherification conditions in the presence of a strong acid catalyst selected from:
  (1) a cationic resin;
  (2) a β-zeolite;
  (3) dealuminized Y-zeolites; and
  (4) metal-modified β-zeolites.

27 Claims, No Drawings

ISOPROPYL T-BUTYL ETHER (IPTBE) GENERATION FROM CRUDE ACETONE

CROSS-REFERENCE

This application is related to U.S. application Ser. No. 08/148,244 and 08/188,007. It is also related to U.S. Pat. Nos. 4,822,921; 4,827,048; 5,099,072; 5,081,318; 5,059,725; 5,157,162; 5,162,592; 5,157,161; 5,183,947; and allowed U.S. Ser. Nos. 07/917,218, now U.S. Pat. No. 5,214,217; 07/878,121, now U.S. Pat. No. 5,214,218; and 07/917,885, now U.S. Pat. No. 5,220,078, all of which are incorporated by reference herein in their entirety.

FIELD OF THE INVENTION

This invention concerns a novel two-step procedure for generation of isopropyl t-butyl ether (IPTBE), and optionally methyl t-butyl ether (MTBE), from a crude by-product acetone stream which comprises (1) hydrogenating the crude acetone stream over a bulk-metal nickel-rich catalyst to give an isopropanol-rich effluent; and (2) subjecting the isopropanol-rich intermediate to etherification conditions in the presence of a series of strong acid catalysts selected from the group consisting of cationic resins, $\beta$-zeolites, metal-modified $\beta$-zeolites and dealuminized Y-zeolites to yield a mix of IPTBE and MTBE.

IPTBE is useful as an octane enhancer in gasoline.

BACKGROUND OF THE INVENTION

It is known to those skilled in the art that ethers, including both symmetrical and unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

An article titled "Expanding Refinery Technology leads to New Ether Potential," by William J Peil, *Fuel Reformulation*, (1992, November/December) p. 34 contains a good review of the potential of ethers other than MTBE for use in meeting the EPA's requirements.

Though MTBE is the most widely produced and discussed ether, other ethers are also being evaluated, such as diisopropyl (DIPE) and ethyl tertiary butyl ether (ETBE). DIPE can be produced from refinery propylene and water and isopropanol is an intermediate in this process. In a variation, isopropyl tertiary butyl ether could be produced by combining isobutylene with isopropanol.

The higher molecular weight ethers all have blending vapor pressures lower than MTBE, and much lower than ethanol. Their boiling temperatures are also higher than MTBE. Furthermore, higher molecular weight IPTBE and ETBE have the potential to contribute more octane. As the graph, Ibid, p. 36 illustrates, IPTBE has the capability of providing the greatest net octane increase, (R+M)/2, of all the oxygenates considered here as fuel additives to gasoline. In addition, because of their lower oxygen content, more volume of the higher MW ethers, such as IPTBE, can be added to base gasoline without exceeding the target oxygen content.

Although there has not been as much discussion regarding the production of IPTBE as there has been for MTBE, it is apparent that with its lower oxygen level and lower vapor pressure, there should be a definite niche for IPTBE in the future of reformulated gasoline.

With regard to classes of solid acid catalysts found suitable in this invention for IPTBE synthesis one of the earliest disclosures of zeolite beta was in U.S. Pat. No. 3,308,069 (1967) to Wadinger et al.

J. B. Higgins, et al. of Mobil Research and Development published an article in *Zeolites*, 1988, Vol. 8, November, 446–452 titled "The Framework Topology of Zeolite Beta." In the article Higgins et al. disclose what is known about the framework topology of zeolite beta. The information has been determined using a combination of model building, distance-least-square refinement and powder pattern simulation.

In an article titled "Cumene Disproportionation over Zeolite $\beta$ I. Comparison of Catalytic Performances and Reaction Mechanisms of Zeolites," *Applied Catalysis*, 77 (1991) 199–207, Tseng-Chang Tsai, Chin-Lan Ay and Ikai Wang disclose a study demonstrating that cumene disproportionation can be applied as a probe reaction for zeolite structure. It is revealed that zeolite beta would have application potential in the production of diisopropylbenzene for reasons of activity, selectivity and stability.

In a second part of the article, "II. Stability Enhancement with Silica Deposition and Steam Pretreatment", Ibid, pp. 209–222, Tsai and Wang disclose their development of two methods to improve the stability of zeolite beta, silica deposition and steam pretreatment.

Patents in the art which employ zeolite beta relate mainly to dewaxing, and cracking of hydrocarbon feedstock.

An article titled "Beta Zeolite as Catalyst or Catalyst Additive for the Production of Olefins During Cracking or Gas Oil," was written by L. Bonetto et al, 9th International Zeolite Conference, July 1992, FP 22. The authors note that with the greater demand for oxygenated compounds there is indication there might be increased demands for catalysts and conditions which maximize $C_3$, $C_4$ and $C_5$ olefins. They suggest that $\beta$-zeolite could be used alone or combined with Y-zeolite as a suitable zeolite component. Various catalysts were studied with respect to minimization of diffusional requirements and zeolite stability.

U.S. Pat. No. 4,419,220, to Mobil, discloses a process for dewaxing a hydrocarbon feedstock containing straight chain paraffins which comprises contacting the feedstock with a $\beta$-zeolite beta catalyst having a Si:Al ratio of at least 30:1 and a hydrogenation component under isomerization conditions.

Another European Application to Mobil, EP 0 094 82, discloses simultaneous catalytic hydrocracking and hydrodewaxing of hydrocarbon oils with $\beta$-zeolite.

In European Patent Application 0 095 303, to Mobil, there is a disclosure of dewaxing distillate fuel oils by the use of $\beta$-zeolite catalysts which, preferably have a silica:alumina ratio over 100:1. Ratios as high as 250:1 and 500:1 are disclosed as useful.

Another U.S. Pat. No. 4,518,485, to Mobil, discloses a process for dewaxing a hydrocarbon feedstock containing paraffins selected from the group of normal paraffins and slightly branched paraffins and sulfur and nitrogen compounds where, after conventionally hydrotreating the feedstock to remove sulfur and nitrogen, the hydrotreated feedstock is dewaxed by contacting the feedstock with a catalyst comprising a $\beta$-zeolite having a silica/alumina ratio of at least 30:1.

In U.S. Pat. No. 4,740,292, to Mobil, there is disclosed a catalytic cracking process which comprises cracking a hydrocarbon feed in the absence of added hydrogen with a cracking catalyst comprising a β-zeolite component and a faujasite component comprising at least one crystalline aluminosilicate of the faujasite structure, the weight ratio of the faujasite component to the β-zeolite component being from 1:25 to 20:1.

Large pore β-zeolite has been employed in the synthesis of industrially important para-cumene by toluene isopropylation. See "Toluene Isopropylation over Zeolite β and Metallosilicates of MFI Structure," P. A. Parikh et al., *Applied Catalysis, A*, 1992, 90, p. 1.

In European Patent 323 138 and U.S. Pat. No. 4,906,787, there is disclosed a catalytic process for converting light olefins to ethers suitable as high octane blending stocks carried out by contacting the olefin, especially propene, with water and alcohol recovered from a downstream distillation operation in an olefin conversion unit in the presence of an acidic zeolite catalyst. In this work diisopropyl ether (DIPE) was prepared from $C_3H_6$ and aqueous iso-PrOH in the presence of silica-bound zeolite Beta catalyst at 166°.

Another European Patent, EP 323 268, light olefins are converted to alcohols and/or ethers in the presence of β-zeolite.

A number of references discuss the use of faujasite zeolites in various applications.

Japanese Patent 82-07432 teaches the use of zeolites, particularly mordenites and faujasites, to make dialkyl ethers containing primary or secondary alkyl groups by the liquid phase dehydration of alcohols.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In allowed U.S. patent application Ser. No. 07/917,218, there is disclosed a method for preparing methyl tertiary butyl ether by reacting butanol and methanol in the presence of a catalyst comprising a super-acid alumina or a faujasite-type zeolite.

In U.S. Pat. No. 5,081,318, a Y-type zeolite modified with fluorosulfonic acid is disclosed.

In U.S. Pat. No. 3,955,939, to Sommer et al. (1976), there is disclosed the production of a water-free mixture of isopropyl alcohol, diisopropyl alcohol, diisopropyl ether and by-products by the catalytic hydration of propylene in the gaseous phase at temperatures of 140°-170° C., wherein the water-free mixture formed according to the process can be used directly as an additive to gasoline fuel.

None of the available references would seem to suggest the conversion of the acetone portion present in a by-product stream into IPTBE. The portion of said by-product stream which typically comprises acetone is about 10% to 80%. It would greatly enhance the economics of any process to produce oxygenates if acetone from a by-product stream could be converted to useful oxygenate products such as isopropyl tertiary butyl ether, as well as methyl tertiary butyl ether (MTBE).

SUMMARY OF THE INVENTION

In accordance with the foregoing the novel method of the instant invention for generation of isopropyl tertiary butyl ether from a crude by-product acetone stream is a two-step process which comprises:

(1) hydrogenating the crude acetone stream over a bulk-metal nickel-rich catalyst to give an isopropanol rich effluent; and
(2) Etherifying the isopropanol-rich intermediate in the presence of a series of strong acid zeolite catalysts selected from the group consisting of cationic resins, β-zeolite, metal-modified β-zeolites and dealuminized Y-zeolites to yield isopropyl tertiary butyl ether (IPTBE).

DETAILED DESCRIPTION OF THE INVENTION

Cogeneration of isopropyl tertiary butyl ether along with methyl t-butyl ether may also be accomplished in the instant invention by the steps listed above, where the by-product acetone stream, in addition, contains significant quantities—that is preferably greater than 5%—of both methanol (MeOH) and t-butanol (tBA). Most preferably, for the cogeneration of IPTBE and MTBE, the crude acetone feed contains 10%-40% each of both methanol and t-butanol.

The two-step IPTBE synthesis can be represented by:

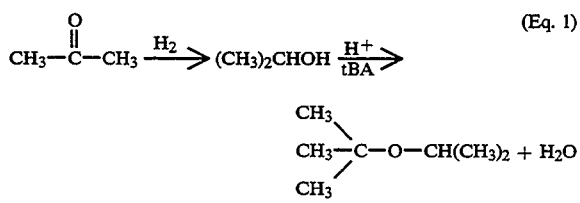

(Eq. 1)

In a process to make propylene oxide a large number of by-products are typically generated with the desired product. The by-products may include formic acid, acetic acid, their ester derivatives, t-butanol and acetone. The acetone may constitute about 10% to 80% of certain crude by-product streams. These crude acetone streams may be further mixed with methanol.

In the first step of the instant invention the crude acetone is passed over a nickel-rich catalyst. A preferred nickel catalyst is characterized by having the composition, calculated in mol %, of from about 60%-85% nickel, 1%-30% copper and 0.1%-6% chromium with the preferred proportions being about 65%-78% nickel, 10%-20% copper and 1%-3% chromium. The temperature necessary to achieve the desired acetone hydrogenation to isopropanol (IPA) is >100° C., the preferable range is 120°-180° C.

The conversion of acetone to isopropanol in the first step of Eq. 1 is normally >90% per pass in continuous processing and preferably it is as great as 99% or more. In the second step the isopropanol is subjected to etherification conditions in the presence of a series of solid strong acid catalysts, from the group consisting of cationic resins, β-zeolite, metal-modified β-zeolites and a dealuminized Y-zeolite.

The ion exchange resins used as catalysts comprise a class of ion exchange resins having a strongly acidic cation exchange. These include the gel type, or macroreticular ion exchange resin, with sulfonic acid ($—SO_3H$), or substituted sulfonic acid functional groups, wherein the sulfonic acid functional group is bonded directly or indirectly to an organic, preferably polystyrene or styrene-divinylbenzene polymer backbone. Examples of such resins include AMBERLYST®-15 and XN-1010, AMBERLITE® IR-118, DOWEX® 50X2-100 and 5X8-100, DOWEX® M-31 and M-32, plus BIO RAD® AG50W-X2 and AMBERSEP® 252H. Another suitable ion exchange resin is Rohm and Haas' A-35 high temperature resin, as well as DuPont's NAFION® resin, having the perfluorosulfonic acid functionality. Preferred are the macroporous resins with the styrene-divinylbenzene polymer backbone, sulfonic acid functionality, and 1%-20% cross-linking, such as AMBERLYST® 15 and XN-1010. Said resins should be in the acid (hydrogen) form.

The second group of exemplified catalysts includes β-zeolite, alone or modified.

The composition of zeolite beta is described in U.S. Pat. Nos. 3,308,069; 4,419,220; 4,518,485 and 4,740,292. In those references, zeolite beta is typically described as follows:

Zeolite beta is a crystalline aluminosilicate having a pore size greater than 5 Angstroms. The composition of the zeolite, as described in U.S. Pat. No. 3,308,069, in its as synthesized form may be expressed as follows:

$[XNa(1.0 \pm 0.1\text{-}X)TEA]AlO_2 \cdot YSiO_2 \cdot WH_2O$ where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

As discussed in the J. B. Higgins, et al. reference, supra, p. 446, the first clues to the crystal structure of zeolite beta were evidenced from chemical and physical property measurements. Ion-exchange isotherms of Na-β at 25° C. indicated that cations as large as tetraethylammonium (TEA+) exchanged completely into the pore system. This behavior suggests that beta contains at least 12-membered rings opening into channels, because TEA+ is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6-19.4 wt % and a measured density of 1.61 g/cm³ ruled out undimensional pore systems such as those in ZSM-12, ZSM-22, ZSM-23 and ZSM-48. Structural similarities among beta, mordenite and ZSM-12 were suspected because all three may be synthesized in Na+-TEA+ systems from highly siliceous batch compositions. Further, zeolite beta is easily synthesized in the SiO₂/Al₂O₃ range of 30-50. This lies between TEA+ mordenite (typically 10-30) and ZSM-12 (typically, >60), suggesting the beta framework contains large fractions of both 4- and 5-membered rings.

In the Tsai and Wang reference, supra, part II, p. 209, stability enhancement is discussed. Two methods, silica deposition and steam pretreatment, have been developed to substantially improve zeolite beta stability.

Ibid, p. 215, it is stated that zeolite beta has two types of three dimensional pore openings, the linear and the tortuous channel. The former has pore openings of 7.5 Å×5.7 Å and the latter has pore openings of 6.5 Å×5.6 Å. When silica, for example, is deposited on zeolite beta, the pore opening was narrowed or blocked by the deposited silica. It was concluded that silica deposition selectively removes strong acid sites and increases the population of medium acid sites.

In the fully base-exchanged form, zeolite beta has the composition:

$[(X/n)M(1 \pm 0.1\text{-}X)H]AlO_2 \cdot YSiO_2 \cdot WH_2O$ where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. No. 4,419,220.

Zeolite beta is characterized by the following X-ray diffraction pattern:

d Values of reflection in zeolite beta
11.40±0.2
7.40±0.2
6.70±0.2
4.25±0.1
3.97±0.1
3.00±0.1
2.20±0.1

The preferred forms of zeolite beta are the highly acidic, high silica forms, having silica-to-alumina mole ratio of at least 10:1, and preferably in the range of 10:1 to 50:1 in the as-synthesized form, and a surface area of at least 100 m²/g. Suitable β-zeolites for the practice of this invention include Valfor C806β, Valfor CP815β and Valfor C861. Valfor® is the registered trademark of the PQ corporation. Valfor® C806β zeolite is zeolite beta powder in template cation form. It is a high silica shape selective zeolite which contains the organic template used in the crystallization step, having been isolated after filtration and washing of the synthesis product. C806β has a SiO₂/Al₂O₃ molar ratio of 23-26; the crystal size is 0.1-0.7 um; the surface area after calcination is about 700-750 m²/g; the cyclohexane adsorption capacity after calcination is 19-24 g/100 g; Na₂O content is about 0.01-1.0% by weight anhydrous; and, the organic content is about 11-13% by weight, on a water-free basis.

Valfor® C815β zeolite is a calcined zeolite beta powder in hydrogen, sodium form. It is similar to C806β except the product has been calcined to decompose the organic template. C815β is a high silica, shape selective aluminosilicate with a large pore diameter. C815β also has a SiO₂/Al₂O₃ molar ratio of about 23-26; the crystal size, surface area, cyclohexane adsorption capacity and Na₂O are all within the same ranges as given for C806β, Valfor® C861β is an extrudate made of 80% C815β powder and 20% alumina powder.

Said β-zeolites may optionally be pretreated before modification with a halogen, a halogen-containing organic compound, or a halogen-containing acid. Said halogen may be fluorine, chlorine, bromine or iodine, but is preferably fluorine. In the case of fluoride treatment, the fluoride content of the treated β-zeolite may be in the range of 0.1 to 10 wt %, but preferably is about 1%. Said fluoride-treated zeolites may optionally be calcined, at temperatures of 200° C. and above, prior to further usage or modification.

Said catalysts may be formed in the presence of a binder, such as Group III or Group IV oxide. Group IV oxides used in conjunction with said β-zeolite include oxides of aluminum, silicon, titanium, zirconium, hafnium, germanium, tin and lead, as well as combinations thereof. Alumina is preferred. Said binders may comprise 10% to 90% of the formed catalyst.

Particularly effective in the subject cogeneration of IPTBE and MTBE are the β-zeolites modified with multiple metals.

The metals useful for modifying the zeolite in the instant invention comprise those from Groups IB, VB, VIB, VIIB and VIII of the Periodic Table, including said transition metals. Preferred metals are those found in Groups IB, VIB, VIIB and VIII of the Periodic Table and include copper, chromium, manganese, iron, nickel, palladium and platinum. Especially good results were observed using combinations of iron, manganese and chromium, or combinations of nickel and copper on VALFOR ® Zeolite 861β, as well as platinum, or palladium, fluoride-modified β-zeolites.

Said zeolites are preferably impregnated with said specified metals as their salts, particularly their metal nitrate or chloride salts, in an aqueous, alcoholic, or ketonic media over a period of 1-24 hours, then the solids are filtered off, dried at elevated temperature, e.g. 120° C., for a period of time and calcined at 300°-800° C. for a further period, e.g. 315° C. for 2 hours, followed by 540° C. for another 2 hours, then reduced in a stream of hydrogen at ≧200° C.

The amount of the various metals deposited on the zeolite can vary. The amount of each individual metal, i.e., iron, chromium, copper, manganese, and nickel, can vary from 0.01 to 10.0%. Where iron, chromium and manganese are deposited on 861β the preferred weight percent is from 0.1% to 5.0%.

The fourth type of catalyst suitable for the second stage of this invention generally comprises dealuminated Y-zeolite catalysts.

The preferred catalysts for use in the dealuminated form for the reaction of Eq. 1 are certain crystalline aluminosilicate zeolites, particularly the isostructural group of faujasite zeolites that include the synthetic X- and Y-zeolites. The preferred zeolites for dealumination are the Y-zeolites.

The unit cells of faujasite zeolites are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$$Na_{56}[(AlO_2)_{56}(SiO_2)_{136}]x \cdot 250\ H_2O$$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48, resulting in a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms(designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of $\approx 1.3$ nm, and it can be entered through four distorted 12-member rings of diameter 0.80-0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal. From the catalytic viewpoint, the α-cages are by far the most important, since, unlike the β-cages, they permit entry of numerous aliphatic and aromatic compounds.

It has been demonstrated in the instant invention these Y-zeolites are particularly effective in the dealuminated form. Preferably, said Y-zeolites are dealuminated by ammonium exchange followed by calcination, or by treatment with ethylenediaminetetraacetic acid (EDTA) or other chelating agents, or by treatment with fluorine or a fluorine-containing compound such as silicon tetrafluoride or ammonium fluorosilicate, or hydrothermal (steam) treatment and/or acid treatment. Said dealuminated Y-zeolites should have a silica-to-alumina molar ratio of greater than three, preferably a ratio of 5 or greater. The examples demonstrate the usefulness of catalysts having a silica-to-alumina ratio of 5 to 100.

Examples of suitable commercially available dealuminized Y-zeolites include UOP's LZY-82 and LZY-72, PQ Corporation's CP-304-37 and CP-316-26, UOP's Y-85, Y-84, LZ-10 and LZ-210.

The unit cell size and $SiO_2/Al_2O_3$ molar ratio for typical dealuminated Y-zeolites are noted in the following table:

| ZEOLITE TYPE | UNIT CELL SIZE, A | $SiO_2/Al_2O_3$ MOLAR |
|---|---|---|
| LZY-82 | 24.53 | 7.8 |
| LZY-85 | 24.49 | 9.1 |
| LZY-10 | 24.32 | 23.7 |
| LZY-20 | 24.35 | 18.9 |
| LZY-84 | 24.51 | 8.4 |
| LZ-210 | 24.47 | 9.9 |
| LZY-72 | 24.52 | 8.1 |
| CP316-26 | 24.26 | 45.7 |

Said catalysts may be in the form of powders, pellets, granules, spheres, shapes and extrudates. The examples described herein demonstrate the advantages of using extrudates.

The reaction may be carried out in either a stirred slurry reactor or in a fixed bed continuous flow reactor.

The catalyst concentration should be sufficient to provide the desired catalytic effect.

Etherification to IPTBE can generally be conducted at temperatures from 20° to 250° C.; the preferred range is 40° to 80° C. Good results are observed throughout this temperature range. However, it can be noted that the best conversion figures for IPTBE and MTBE cogeneration are observed when the temperature is 20°–100° C. The total operating pressure may be from 0 to 5000 psig, or higher. The preferred pressure range is 100 to 1000 psi.

Typically, IPTBE is generated continuously in up to ca. 15 wt % concentration or greater in the crude liquid product at total liquid hourly space velocities (LHSV) of up to 6 or higher and relatively mild conditions, where:

$$LHSV = \frac{\text{Volume of Total Liquid Feed Run Through The Reactor Per Hour}}{\text{Volume of Catalyst In Reactor}}$$

Conversions of isopropanol (IPA) are estimated in the following examples using the equation:

$$\frac{(\text{Mole \% of } IPA \text{ in Feed} - \text{Mole \% of } IPA \text{ in Product})}{\text{Mole \% of } IPA \text{ in Feed}} \times 100$$

The examples which follow illustrate the two-step synthesis of IPTBE and MTBE from acetone, also containing methanol plus t-butanol, using cationic resins, β-zeolites, metal-modified β-zeolites and dealuminized Y-zeolites.

The accompanying examples illustrate:

1. The hydrogenation of a crude acetone by-product stream from a MTBE/PO Unit over a bulk metal, nickel-rich, catalyst under moderate conditions (see Example 1).
2. The cogeneration of IPTBE/MTBE from the hydrogenated acetone stream of Example 1 under mild conditions using a β-zeolite catalyst (see Example 2).
3. The cogeneration of IPTBE/MTBE from the hydrogenated acetone stream of Example 1 under mild conditions using a cationic resin catalyst (see Example 3).
4. The generation of IPTBE from an equimolar isopropanol/t-butanol mixture under mild conditions using a β-zeolite or cationic resin catalyst (see Examples 4 and 5).
5. The cogeneration of IPTBE/MTBE from another hydrogenated acetone (73%) stream by passage over a β-zeolite, or cationic resin catalyst (see Examples 6 and 7).
6. The generation of IPTBE from a third hydrogenated acetone (15%) stream by passage over a β-zeolite or cationic resin catalyst (see Examples 8 and 9).

7. IPTBE generation from the hydrogenated acetone stream of Examples 8 and 9, using as the catalyst:
   a) A platinum-impregnated β-zeolite (Example 10).
   b) A palladium-impregnated, fluorided β-zeolite (Example 11).
   c) A chromium, manganese, iron-modified β-zeolite (Example 12).
   d) A nickel, copper-treated β-zeolite (Example 13).
   e) A dealuminized Y-zeolite (Example 14).

EXAMPLE 1

This example illustrates the hydrogenation of a crude acetone stream.

A crude acetone mix from a PO/MTBE unit containing 62% acetone ($Ac_2O$) and having the composition shown in Table 1 was passed, upflow, over a nickel, copper, chromium bulk metal catalyst containing about 72% nickel in the presence of hydrogen (90 l/hr) at LHSV of 0.5 at a series of temperatures (120°–160° C.). Hydrogenation of said stream was achieved at 160° C. and a typical product composition for the liquid fraction is given in Table 1.

Estimated acetone conversion is 99%.

The primary product is isopropanol (IPA). Other organic oxygenates identified in this product fraction include methanol (MeOH), t-butanol (tBA), t-butyl formate (tBF) and allyl t-butyl peroxide (ATBP).

TABLE I

| | | | | | | | | | | |
|---|---|---|---|---|---|---|---|---|---|---|
| CRUDE ACETONE HYDROGENATION | | | | | | | | | | |
| | | Temp. | | | Composition (%)[a] | | | | | |
| Ex. | Catalyst | (°C.) | LHSV | Sample | MeOH | $Ac_2O$ | IPA | tBA | tBF | ATBP |
| 1 | Ni 2715 ⅛" T | | | FS-1 | 13.9 | 61.7 | 0.1 | 16.7 | 0.1 | 3.3 |
| | | 160 | 0.5 | 1 | 15.8 | 0.8 | 48.3 | 30.8 | — | — |

[a]Designations: Methanol (MeOH), Acetone ($Ac_2O$), Isopropanol (IPA), t-Butanol (tBA), t-Butyl Formate (tBF), Allyl t-Butyl Peroxide (ATBP).

EXAMPLE 2

This example illustrates the cogeneration of isopropyl t-butyl ether (IPTBE) and methyl t-butyl ether (MTBE) from a hydrogenated acetone feedstock.

Synthesis was conducted in a tubular reactor (⅜" i.d., 12" long) constructed of 316 stainless steel, operated upflow, and mounted in a furnace, controllable to ±1.0° C., and fitted with pumps allowing flow control to <1± cc/hr. The reactor was also fitted with a pressure regulating device and equipment for monitoring temperature, pressure, and flow rate.

The reactor was charged at the beginning of the experiment with 50 cc of β-zeolite (80% beta, 20% alumina binder, in 1/16" diameter extruded form). A glass wool screen was placed at the top and bottom of the reactor to ensure the catalyst would remain in the middle portion.

The catalyst bed was treated with the crude hydrogenated acetone feedstock of Example 1, while the reactor was held at a series of temperatures (40°–100° C.). Total unit pressure was maintained at about 700 psi. Samples of crude product effluent were collected periodically on stream, in 316 ss bombs, and analyzed by glc and gc-ms. Typical analyses data are summarized in Table 2. At 80° C.:

The t-butanol conversion level is 41% (Sample 6).
The MTBE molar selectivity is 76%.
The IPTBE molar selectivity is 16%.

Some diisopropyl ether (DIPE), isobutylene, diisobutylene ($C_8H_{16}$) and water were also generated as coproducts of this etherification.

Product identification was by a combination of gc-ms and glc techniques.

EXAMPLE 4 AND 5

These examples illustrate the generation of isopropyl t-butyl ether from a mixture of t-butanol and isopropanol.

TABLE 2

IPTBE SYNTHESIS
PRODUCT COMPOSITION (Wt %)

| Ex. | Catalyst | Temp. (°C.) | Sample | DME | $C_4H_8$ | MeOH | $Ac_2O$ | IPE | IPA | tBA | MTBE | IPTBE | IBA | $C_8H_{16}$ | -METHOD 26- $H_2O$ |
|---|---|---|---|---|---|---|---|---|---|---|---|---|---|---|---|
| 2 | C861β[a] | | Feed | — | — | 15.9 | 0.8 | 48.2 | 30.8 | 0.1 | — | — | 3.0 | — | 5.6 |
| | | 40 | 1 | — | 0.1 | 15.4 | 0.8 | 48.1 | 30.7 | 0.7 | 0.1 | 0.5 | 2.9 | — | 5.9 |
| | | | 2 | | 0.1 | 15.3 | 0.8 | 47.8 | 30.8 | 0.7 | 0.1 | 0.6 | 2.9 | | 5.6 |
| | | 60 | 3 | — | 0.5 | 14.8 | 0.8 | 47.8 | 27.8 | 2.5 | 0.1 | 1.7 | 2.8 | — | 6.3 |
| | | | 4 | — | 0.5 | 14.9 | 0.8 | 47.9 | 27.6 | 2.4 | 0.1 | 1.7 | 2.8 | 0.1 | 6.4 |
| | | 80 | 5 | — | 1.5 | 11.7 | 0.9 | 48.7 | 18.4 | 11.3 | — | 3.0 | 2.6 | 0.1 | 8.7 |
| | | | →6 | — | 1.5 | 11.7 | 0.9 | 48.7 | 18.2 | 11.4 | 0.1 | 3.1 | 2.6 | 0.1 | 8.8 |
| | | 100 | 7 | 0.1 | 2.6 | 11.3 | 0.9 | 48.9 | 14.2 | 13.3 | 0.1 | 3.1 | 2.6 | 0.8 | 9.5 |
| | | | 8 | 0.1 | 2.6 | 11.2 | 0.9 | 48.9 | 14.2 | 13.3 | 0.1 | 3.1 | 2.6 | 0.8 | 9.5 |

[a] Run at LHSV 0.5, 700 psi

EXAMPLE 3

This example illustrates the cogeneration of isopropyl t-butyl ether (IPTBE) and methyl t-butyl ether (MTBE) from a hydrogenated acetone feedstock.

Synthesis was conducted using the equipment and procedures of Example 2. The reactor was charged with 50 cc of Amberlyst® A-15 (a sulfonated, styrene-divinylbenzene resin in bead form, presoaked in isopropanol) and the catalyst bed was treated with the crude hydrogenated acetone feedstock of Example 1, at a series of temperatures (40°-100° C.).

Typical analyses results are summarized in Table 3. At 80° C.:

The t-butanol conversion level is 47% (Sample 6).
The MTBE molar selectivity is 81%.
The IPTBE molar selectivity is 14%.

Syntheses were conducted using the equipment and procedures of Example 2. The reactor was charged with 50 cc of catalyst (either β-zeolite or cationic resin) and the catalyst bed was treated with a 1:1 molar mix of t-butanol and isopropanol over a range of temperatures (40°-140° C.) and LHSV's (0.25→4).

Typical results are summarized in Tables 4 and 5.

At 60° C., using β-zeolite (C861β) as catalyst:
The t-butanol conversion is 25%.
IPTBE effluent concentration is 14.4%.

At 60° C., using cationic resin (A-15) as catalyst:
The t-butanol conversion is 24%.
IPTBE effluent concentration is 15.3%.

Significant quantities of diisopropyl ether (DIPE) and diisobutylene ($C_8H_{16}$) were generated at the higher operating temperatures (100°-140° C.). Product identification was by gc-ms and glc techniques.

TABLE 3

IPTBE SYNTHESIS
PRODUCT COMPOSITION (Wt %)

| Ex. | Catalyst | Temp. (°C.) | Sample | DME $C_8H_{16}$ | $C_4H_8$ | MeOH | $Ac_2O$ | IPE | IPA | tBA | MTBE | IPTBE | IBA | -METHOD 26- $H_2O$ |
|---|---|---|---|---|---|---|---|---|---|---|---|---|---|---|
| 3 | A-15[a,b] | Feed | Feed | — | — | 15.7 | 0.8 | 48.2 | 30.9 | 0.1 | — | — | 3.0 | 5.7 |
| | | 40 | 1 | — | 0.7 | 15.0 | 0.8 | 48.2 | 28.4 | 2.3 | 0.1 | 0.9 | 2.9 | 6.4 |
| | | | 2 | | 0.6 | 15.1 | 0.8 | 48.4 | 28.0 | 2.3 | 0.1 | 0.9 | 2.9 | 6.6 |
| | | 60 | 3 | — | 0.9 | 12.2 | 0.8 | 48.8 | 19.2 | 10.6 | 0.1 | 3.3 | 2.8 | 8.6 |
| | | | 4 | — | 0.9 | 12.1 | 0.8 | 48.8 | 19.4 | 10.4 | 0.1 | 3.2 | 2.7 | 8.5 |
| | | 80 | 5 | — | 1.3 | 10.9 | 0.9 | 49.2 | 15.8 | 14.2 | 0.1 | 3.0 | 2.5 | 9.4 |
| | | | →6 | — | 1.3 | 10.8 | 0.9 | 48.8 | 16.5 | 13.9 | 0.1 | 3.2 | 2.5 | 9.2 |
| | | 100 | 7 | 0.1 | 2.2 | 11.0 | 0.9 | 48.1 | 15.1 | 13.4 | 0.4 | 3.0 | 2.4 | 9.1 |
| | | | 8 | 0.1 | 2.2 | 11.0 | 0.9 | 48.3 | 15.1 | 13.3 | 0.4 | 3.0 | 2.4 | 9.0 |

[a] Presoaked in isopropanol.
[b] Run at LHSV 0.5, 700 psi.

TABLE 4

IPTBE SYNTHESIS
PRODUCT COMPOSITION (%)

| Ex. | Catalyst | Temp. (°C.) | LHSV | Time (Days) | Sample | $C_3H_6$ | $C_4H_8$ | 2-PrOH | tBA | DIPE | IPTBE | $C_8H_{16}$ | METHOD $H_2O$ |
|---|---|---|---|---|---|---|---|---|---|---|---|---|---|
| 4 | C861β | — | — | — | FS-1 | — | — | 33.0 | 66.8 | — | — | — | — |
| | | 100 | 0.5 | 1 | 1 | c | 5.4 | 30.7 | 19.4 | 0.6 | 3.9 | 24.7 | 8.9 |
| | | | | | 2 | | 0.1 | | | | | | 10.3 |
| | | 120 | — | 2 | 3 | 0.8 | 2.7 | 25.0 | 6.1 | 5.7 | 1.1 | 23.4 | 11.9 |
| | | | | | 4 | 1.0 | 2.7 | 24.3 | 5.4 | 6.4 | 0.9 | 23.0 | 12.0 |
| | | 140 | — | 3 | 5 | 5.5 | 0.6 | 10.6 | 1.5 | 16.6 | 0.2 | 21.9 | 13.1 |
| | | | | | 6 | 5.6 | 0.6 | 9.7 | 0.9 | 16.9 | 0.2 | 21.7 | 13.1 |
| | | 60 | — | 4 | 7 | — | 5.3 | 28.5 | 50.4 | 0.1 | 14.3 | 0.7 | 4.0 |
| | | | | | →8 | | 5.4 | 28.2 | 50.3 | 0.2 | 14.4 | 0.7 | 4.1 |

TABLE 4-continued

IPTBE SYNTHESIS

| Ex. | Catalyst | Temp. (°C.) | LHSV | Time (Days) | Sample | PRODUCT COMPOSITION (%) METHOD 27 | | | | | | | METHOD H₂O |
|---|---|---|---|---|---|---|---|---|---|---|---|---|---|
| | | | | | | C₃H₆ | C₄H₈ | 2-PrOH | tBA | DIPE | IPTBE | C₈H₁₆ | |
| | | 80 | — | 5 | 9 | — | 8.1 | 28.8 | 44.5 | 0.1 | 12.3 | 5.0 | 5.3 |
| | | | | | 10 | | 7.9 | 28.7 | 43.9 | 0.1 | 12.2 | 5.3 | 5.5 |
| | | 60 | 0.25 | b | 11 | — | 5.4 | 28.3 | 50.1 | 0.1 | 14.7 | 0.9 | 4.6 |
| | | | | | 12 | | 5.4 | 28.3 | 50.3 | 0.1 | 14.7 | 0.9 | 4.3 |
| | | 80 | — | 7 | 13 | —· | 7.4 | 29.1 | 43.7 | 0.1 | 11.7 | 6.6 | 5.7 |
| | | | | | 14 | | 7.3 | 29.3 | 43.8 | 0.1 | 11.7 | 6.7 | 5.8 |
| | | 40 | — | 8 | 15 | — | 1.5 | 30.9 | 60.6 | — | 6.7 | 0.1 | 1.5 |
| | | | | | 16 | | 1.6 | 30.8 | 60.2 | 0.1 | 7.0 | 0.1 | 1.6 |

<sup>a</sup>No analyses data.

TABLE 5

IPTBE SYNTHESIS

| Ex. | Catalyst | Temp. (°C.) | LHSV | Time (Days) | Sample | PRODUCT COMPOSITION (%) METHOD 27 | | | | | | | METHOD H₂O |
|---|---|---|---|---|---|---|---|---|---|---|---|---|---|
| | | | | | | C₃H₆ | C₄H₈ | 2-PrOH | tBA | DIPE | IPTBE | C₈H₁₆ | |
| 5 | A-15ᵃ | — | — | — | FS-1 | — | — | 32.9 | 66.9 | — | — | — | 0.1 |
| | | 40 | 0.5 | 1 | 1 | — | 3.3 | 29.3 | 55.2 | 0.1 | 11.7 | 0.1 | 2.9 |
| | | | | | 2 | | 3.3 | 29.2 | 55.3 | 0.1 | 11.8 | | 2.7 |
| | | 60 | — | — | 3 | — | 4.9 | 28.3 | 51.2 | 0.1 | 15.1 | 0.1 | 3.8 |
| | | | | | →4 | — | 5.2 | 28.2 | 50.8 | 0.1 | 15.3 | 0.1 | 3.8 |
| | | 80 | — | — | 5 | 0.1 | 8.2 | 28.2 | 46.5 | 0.2 | 13.6 | 1.0 | 4.4 |
| | | | | | 6 | 0.1 | 8.2 | 28.6 | 47.4 | 0.2 | 13.9 | 0.8 | 4.5 |
| | | 100 | — | — | 7 | 0.9 | 10.8 | 28.2 | 41.8 | 0.6 | 10.2 | 6.0 | 5.9 |
| | | | | | 8 | 0.9 | 11.0 | 28.4 | 41.4 | 0.6 | 10.3 | 6.1 | 5.9 |
| | | 60 | 1.0 | — | 9 | — | 5.8 | 28.5 | 50.9 | 0.1 | 14.4 | — | 3.7 |
| | | | | | 10 | | 5.9 | 28.4 | 50.7 | 0.1 | 14.5 | 0.1 | 3.7 |
| | | 60 | 4.0 | — | 11 | — | 6.4 | 30.5 | 55.2 | 0.1 | 7.2 | — | 2.7 |
| | | | | | 12 | | 6.4 | 30.8 | 55.3 | 0.1 | 7.1 | | 2.7 |

<sup>a</sup>Presoaked overnight in isopropanol.

EXAMPLES 6 AND 7

These examples illustrate the cogeneration of isopropyl t-butyl ether (MTBE) from a hydrogenated acetone feedstock.

Syntheses were conducted using the equipment and procedures of Example 2. The reactor was charged with 50 cc of catalyst (either β-zeolite or cationic resin) and the catalyst bed was treated with a crude acetone feedstream containing 73% acetone, methyl formate (MeF), methanol (MeOH), t-butanol (tBA), di-t-butyl peroxide (DTBP) plus butanes, that had been hydrogenated by the procedure of Example 1, to convert the acetone fraction to isopropanol (IPA) and then blended with additional t-butanol to a IPA:tBA molar ratio of 1:1. Etherification of this IPA:tBA mix to IPTBE plus MTBE was conducted over a range of operating temperatures. Typical results are summarized in Tables 6 and 7.

At 80° C., using the cationic resin (A-15) as catalyst:
The t-butanol conversion is 34%.
IPTBE molar selectivity is 26%.
AT 80° C., using the β-zeolite (C861β) as catalyst:
The t-butanol conversion is 44%.
IPTBE effluent concentration is 7.3%.

Some isopropyl formate (IPF), isobutylene, diisobutylene (C₈H₁₆) and water were also generated as coproducts during these etherification experiments. Product identification was by a combination of gc-ms and glc techniques.

TABLE 6

IPTBE SYNTHESIS

| Ex. | Catalyst | Temp. (°C.) | Feed Rate (cc/hr) | Sample | PRODUCT COMPOSITION (wt %) METHOD 27 | | | | | | | | | | METHOD 26 | |
|---|---|---|---|---|---|---|---|---|---|---|---|---|---|---|---|---|
| | | | | | C₄H₈ | MeOH+ MeF | IPA | tBA | MTBE | IPF | IPTBE | C₈H₁₆ | DTBP | H₂O | MeF+ | |
| 6 | A-15ᵃ,ᵇ | — | — | FS-1 | — | 20.3 | 26.3ᶜ | 52.6 | — | — | — | — | 0.6 | 0.5 | 15.1 | |
| | | 40 | 12 | 1 | 1.8 | 5.8 | 26.5 | 40.5 | 14.1 | 3.4 | 6.9 | — | 0.8 | 4.6 | 2.3 | |
| | | | | 2 | 1.8 | 5.9 | 26.3 | 40.8 | 13.9 | 3.4 | 6.8 | — | 0.8 | 4.6 | 2.2 | |
| | | 60 | 12 | 3 | 2.4 | 4.0 | 26.8 | 35.7 | 19.0 | 3.6 | 7.3 | — | 0.8 | 5.9 | 2.8 | |
| | | | | 4 | 2.6 | 3.9 | 26.4 | 35.8 | 19.2 | 3.6 | 7.3 | — | 0.8 | 5.8 | 2.8 | |
| | | 80 | 12 | →5 | 4.2 | 4.1 | 25.9 | 34.5 | 18.4 | 3.6 | 7.3 | 0.4 | 0.8 | 5.9 | 4.1 | |
| | | | | 6 | 4.1 | 4.3 | 26.5 | 34.0 | 18.5 | 3.6 | 7.1 | 0.4 | 0.8 | 5.9 | 4.3 | |
| | | 100 | 12 | 7 | 6.0 | 4.4 | 25.9 | 31.0 | 17.3 | 3.5 | 6.7 | 1.9 | 0.7 | 6.1 | 5.8 | |
| | | | | 8 | 5.7 | 6.2 | 23.5 | 33.1 | 16.0 | 3.3 | 6.1 | 2.4 | 0.7 | 6.0 | 5.9 | |

<sup>a</sup>Presoaked in isopropanol.
<sup>b</sup>Run at LHSV 0.25, 700 psi.
<sup>c</sup>IPA:tBA molar ratio 1:1.

TABLE 7

IPTBE SYNTHESIS
PRODUCT COMPOSITION (wt %)
METHOD 27

| Ex. | Catalyst | Temp. (°C.) | Feed Rate (cc/hr) | Sample | C4H8 | MeOH+ MeF | IPA | tBA | MTBE | IPF | IPTBE | C8H16 | DTBP | -METHOD 26- H2O | MeF+ |
|---|---|---|---|---|---|---|---|---|---|---|---|---|---|---|---|
| 7 | C861β | | | FS-1 | 1.5[a] | 10.7 | 29.2[b] | 57.6 | — | — | — | — | 0.7 | — | 7.7 |
| | | 40 | 12 | 1 | 2.6 | 8.8 | 26.5 | 49.2 | 5.0 | 2.4 | 4.6 | — | 0.7 | 2.1 | 5.2 |
| | | | | 2 | 1.6 | 9.2 | 26.0 | 49.4 | 4.8 | 2.4 | 4.6 | — | 0.7 | 1.9 | 5.2 |
| | | 60 | 12 | 3 | 4.2 | 5.5 | 25.8 | 39.1 | 13.6 | 3.2 | 7.4 | 0.2 | 0.8 | 4.4 | 4.2 |
| | | | | 4 | 4.2 | 5.5 | 25.7 | 39.1 | 13.6 | 3.1 | 7.5 | 0.2 | 0.8 | 4.5 | 3.9 |
| | | 80 | 12 | →5 | 6.2 | 4.2 | 25.8 | 32.2 | 17.5 | 3.5 | 7.3 | 1.8 | 0.8 | 6.1 | 5.2 |
| | | | | 6 | 5.8 | 4.1 | 25.9 | 32.6 | 17.3 | 3.5 | 7.3 | 1.8 | 0.8 | 6.1 | 5.1 |
| | | 100 | 12 | 7 | 7.5 | 5.1 | 25.7 | 24.8 | 14.8 | 3.4 | 5.1 | 10.0 | 0.7 | 7.9 | 6.6 |
| | | | | 8 | 7.4 | 5.2 | 25.8 | 25.0 | 14.7 | 3.4 | 5.1 | 9.9 | 0.7 | 7.9 | 6.5 |

[a]n-Butane added to feed in the run.
[b]IPA:tBA molar ratio 1:1.

EXAMPLES 8 AND 9

These examples illustrate the generation of isopropyl t-butyl ether (IPTBE) from a hydrogenated acetone feedstock.

Syntheses were conducted using the equipment and procedures of Example 2. The reactor was charged with 50 cc of catalyst (either β-zeolite or cationic resin) and the catalyst bed was treated with a crude acetone feedstream containing 15% acetone, methyl formate, methanol, isopropanol, t-butanol, di-t-butyl peroxides plus butanes, that had been hydrogenated by the procedure of Example 1 to convert said acetone fraction to additional isopropanol. The IPA:tBA molar ratio or the final feed mix was 1:3.8. Etherification to IPTBE was conducted over a range of temperatures (40°–100° C.). Typical results are summarized in Tables 8 and 9.

At 60° C., using the cationic resin (A-15) as catalyst:
The t-butanol conversion is 12%.
IPTBE molar selectivity is 42%.

At 60° C., using the β-zeolite (C861β) as catalyst:
The t-butanol conversion is 12%.
IPTBE effluent concentration is 6.5%.

Typical IPTBE product was then isolated by fractional distillation of the crude effluent material of Example 9.

TABLE 8

IPTBE SYNTHESIS
PRODUCT COMPOSITION (wt %)
METHOD 27

| Ex. | Catalyst | Temp. (°C.) | Feed Rate (cc/hr) | Sample | C4H8 | MeOH+ MeF | IPA | tBA | MTBE | IPF | IPTBE | C8H16 | DTBP | -METHOD 26- H2O | MeF+ |
|---|---|---|---|---|---|---|---|---|---|---|---|---|---|---|---|
| 8 | A-15[a,b] | | — | FS-1 | 0.9[c] | 3.5 | 11.2[d] | 81.4 | — | — | — | — | 2.8 | 0.1 | 3.1 |
| | | 40 | 12 | 1 | 5.0 | 0.8 | 9.6 | 74.4 | — | 1.0 | 6.0 | 0.1 | 2.9 | 3.8 | 4.6 |
| | | | | 2 | 4.8 | 0.8 | 9.7 | 74.5 | — | 1.0 | 5.9 | 0.1 | 2.8 | 3.9 | 4.4 |
| | | 60 | | →3 | 7.3 | 0.7 | 9.4 | 71.5 | — | 1.0 | 6.5 | 0.3 | 2.9 | 5.0 | 7.4 |
| | | | | 4 | 7.4 | 0.6 | 9.2 | 71.9 | — | 1.0 | 6.5 | 0.2 | 2.9 | 4.8 | 7.4 |
| | | 80 | | 5 | 10.7 | 0.7 | 9.4 | 67.4 | — | 0.9 | 5.8 | 1.6 | 2.9 | 6.3 | 10.8 |
| | | | | 6 | 10.8 | 0.7 | 9.4 | 61.9 | 5.4 | 1.0 | 5.8 | 1.6 | 2.9 | 6.2 | 11.1 |
| | | 100 | | 7 | 13.7 | 0.9 | 9.2 | 53.5 | 6.0 | 0.9 | 4.4 | 6.9 | 2.8 | 7.7 | 13.5 |
| | | | | 8 | 13.9 | 0.9 | 9.2 | 53.5 | 6.0 | 0.9 | 4.4 | 6.9 | 2.8 | 7.6 | 14.1 |

[a]Presoaked in isopropanol.
[b]Run at LHSV 0.25, 700 psi.
[c]Feed contains n-butane.
[d]IPA:tBA molar ratio 1:3.8.

TABLE 9

IPTBE SYNTHESIS
PRODUCT COMPOSITION (wt %)
METHOD 27

| Ex. | Catalyst | Temp. (°C.) | Feed Rate (cc/hr) | Sample | C4H8 | MeOH+ MeF | IPA | tBA | MTBE | IPF | IPTBE | C8H16 | DTBP | -METHOD 26- H2O | MeF+ |
|---|---|---|---|---|---|---|---|---|---|---|---|---|---|---|---|
| 9 | C861β[a] | | — | FS-1 | 0.9[b] | 3.4 | 11.3[c] | 81.2 | 0.1 | 0.1 | — | — | 2.8 | 0.2 | 3.2 |
| | | 40 | 12 | 1 | 3.8 | 2.4 | 9.7 | 75.9 | — | 0.5 | 4.4 | 0.2 | 2.8 | 2.5 | 4.2 |
| | | | | 2 | 3.8 | 2.3 | 9.6 | 76.0 | — | 0.5 | 4.5 | 0.1 | 2.8 | 2.5 | 4.2 |
| | | 60 | | →3 | 7.3 | 0.9 | 9.1 | 71.5 | — | 0.7 | 6.5 | 0.8 | 2.9 | 4.7 | 6.8 |
| | | | | 4 | 7.2 | 1.0 | 9.1 | 71.5 | — | 0.8 | 6.5 | 0.7 | 2.9 | 4.6 | 7.4 |
| | | 80 | | 5 | 9.9 | 0.8 | 9.3 | 65.3 | — | 0.8 | 5.5 | 4.0 | 2.9 | 6.5 | 9.9 |
| | | | | 6 | 9.5 | 0.7 | 9.3 | 60.9 | 5.0 | 0.8 | 5.5 | 4.0 | 3.0 | 6.5 | 9.0 |
| | | 100 | | 7 | 10.0 | 1.1 | 9.6 | 45.8 | 5.8 | 0.7 | 3.5 | 16.4 | 2.9 | 10.6 | 10.3 |
| | | | | 8 | 9.8 | 1.0 | 9.8 | 47.1 | 5.8 | 0.8 | 3.6 | 15.8 | 2.9 | 10.2 | 10.4 |

[a]Run at LHSV 0.25, 700 psi.
[b]Feed contains n-butane.
[c]IPA:tBA molar ratio 1:3.8.

EXAMPLE A

This example illustrates the preparation of platinum-treated β-zeolite.

To a sample of β-zeolite (50% beta, 50% alumina, 1/16" diameter extruded form, 300 cc, 176 g) was added a solution of tetraamine platinum(II) nitrate (Pt(NH$_3$)$_4$(NO$_2$)$_2$, 1.75 g) in 120 cc of distilled water, with stirring. After mixing for up to 1 hour, the solid was dried at 120° C. for 2 hours, calcined at 540° C. for 3 hours, and reduced in a stream of hydrogen at 400° C. for 4 hours.

EXAMPLE B

This example illustrates the preparation of a nickel, copper treated β-zeolite.

To a sample of β-zeolite (80% beta, 20% alumina, 1/16" diameter extruded form, 100 g) was added a solution of nickel nitrate (5.05 g) plus copper nitrate (3.74 g) in distilled water (88 cc), with stirring after mixing for up to 1 hour, the solid was dried at 120° C. for 2 hours, calcined at 315°→480° C. for 12 hours, and reduced in a stream of hydrogen at 350° C. for 4 hours.

EXAMPLE C

This example illustrates the preparation of a chromium, manganese, iron-treated β-zeolite.

To a sample of β-zeolite (80% beta, 20% alumina, 1/16" diameter extruded form, 92 g) was added a solution of ferric chloride (FeCl$_3$.6H$_2$O, 4.57 g), chromium-(III) nitrate (Cr(NO$_3$)$_3$.9H$_2$O, 7.27 g) and manganese nitrate (Mn(NO$_3$)$_2$.6H$_2$O, 4.93 g) dissolved in 90 cc of distilled water, with stirring. After mixing for up to 1 hour, the solid was dried at 120° C., overnight, calcined at 315°→540° C. for 4 hours, and reduced in a stream of hydrogen at 350° C.

EXAMPLES 10–14

These examples illustrate the generation of isopropyl t-butyl ether (IPTBE) from a hydrogenated acetone feedstock.

Syntheses were conducted using the equipment and procedures of Example 2 and the hydrogenated acetone feedstock of Examples 8 and 9. The metal-modified β-zeolite catalysts demonstrated to be effective for IPTBE/MTBE cosynthesis include:

a) The platinum-impregnated β-zeolite of Example A (See Table 10).
b) A palladium-impregnated, fluorided β-zeolite (See Table 10).
c) The chromium, manganese, iron-modified β-zeolite of Example C (See Table II).
d) The nickel, copper-treated β-zeolite of Example D (See Table II).

Isopropyl t-butyl ether generation was also realized with a dealuminized Y-zeolite, CP316-26 from PQ Corp. (See Table 12).

TABLE 10

IPTBE SYNTHESIS
PRODUCT COMPOSITION (wt %)

| Ex. | Catalyst | Temp. (°C.) | Feed Rate (cc/hr) | Sample | C$_4$H$_8$ | MeOH+ MeF | IPA | tBA | MTBE | IPF | IPTBE | C$_8$H$_{16}$ | DTBP | -METHOD 26- H$_2$O |
|-----|----------|------|------|--------|------|------|------|------|------|------|------|------|------|------|
| 10 | Ex. A$^a$ | | 7055-49R-2 | FS-1 | 0.9 | 3.4 | 11.3 | 81.2 | 0.1 | 0.1 | — | — | 2.8 | 0.2 |
| | | 60 | 12 | 1 | 6.3 | 1.5 | 9.3 | 73.0 | — | 0.6 | 5.9 | 0.3 | 2.9 | 4.1 |
| | | | | 2 | 6.6 | 1.3 | 9.3 | 68.3 | 4.2 | 0.6 | 6.0 | 0.5 | 2.9 | 4.4 |
| | | 80 | | 3 | 10.6 | 0.8 | 9.4 | 60.2 | 6.1 | 0.7 | 5.5 | 3.1 | 2.9 | 6.2 |
| | | | | 4 | 10.0 | 0.8 | 9.5 | 61.1 | 5.9 | 0.7 | 5.5 | 2.9 | 2.9 | 6.2 |
| 11 | Pd,F/β$^b$ | | | FS-1 | 0.5 | 2.1 | 11.3 | 82.2 | — | 0.2 | — | — | 2.8 | — |
| | | 60 | 12 | 1 | 6.7 | 1.2 | 9.3 | 67.7 | 4.3 | 0.6 | 6.1 | 0.6 | 2.8 | 4.7 |
| | | | | 2 | 6.6 | 0.9 | 9.4 | 67.8 | 4.7 | 0.6 | 6.0 | 0.5 | 2.8 | 4.6 |
| | | 80 | | 3 | 10.5 | 0.6 | 9.4 | 59.6 | 6.3 | 0.7 | 5.4 | 3.5 | 2.8 | 9.4 |
| | | | | 4 | 9.7 | 0.7 | 9.5 | 60.6 | 6.2 | 0.7 | 5.4 | 3.0 | 2.8 | 9.6 |

$^a$0.3% Pt on 50% beta/alumina, recovered at 400° C.
$^b$0.3 Pd, 1% F, on 50% beta/alumina, recovered at 200° C.

TABLE 11

IPTBE SYNTHESIS
PRODUCT COMPOSITION (wt %)
METHOD 27

| Ex. | Catalyst | Temp. (°C.) | Feed Rate (cc/hr) | Sample | C$_4$H$_8$ | MeOH+ MeF | IPA | tBA | MTBE | IPF | IPTBE | C$_8$H$_{16}$ | DTBP | -METHOD 26- H$_2$O |
|-----|----------|------|------|--------|------|------|------|------|------|------|------|------|------|------|
| 12 | Ex. C$^a$ | | | FS-1 | 0.9 | 3.4 | 11.3 | 81.2 | 0.1 | 0.1 | — | — | 2.8 | 0.2 |
| | | 60 | 12 | 1 | 6.9 | 1.0 | 9.3 | 68.1 | 4.4 | 0.6 | 5.9 | 0.4 | 2.8 | 4.3 |
| | | | | 2 | 6.6 | 1.0 | 9.3 | 68.5 | 4.3 | 0.6 | 5.9 | 0.4 | 2.8 | 4.6 |
| | | 80 | | 3 | 10.7 | 0.7 | 9.4 | 60.8 | 6.2 | 0.7 | 5.6 | 2.2 | 2.9 | 6.4 |
| | | | | 4 | 10.6 | 0.7 | 9.4 | 60.8 | 6.2 | 0.7 | 5.6 | 2.2 | 2.9 | 6.3 |
| 13 | Ex. B$^b$ | | | FS-1 | 0.9 | 3.4 | 11.3 | 81.2 | 0.1 | 0.1 | — | — | 2.8 | 0.2 |
| | | 60 | 12 | 1 | 5.1 | 1.6 | 9.8 | 75.5 | — | 0.4 | 4.4 | 0.1 | 2.0 | 3.1 |
| | | | | 2 | 5.0 | 1.5 | 9.8 | 75.5 | — | 0.4 | 4.4 | 0.1 | 2.1 | 2.9 |
| | | 80 | | 3 | 10.9 | 0.8 | 9.4 | 62.5 | 5.8 | 0.6 | 5.7 | 1.2 | 1.9 | 5.9 |
| | | | | 4 | | | | | | | | | | |

$^a$1% Cr, 1% Mn, 1% Fe on 80% beta, 20% alumina.
$^b$1% Ni, 1% Cr on 80% beta, 20% alumina, reduced at 350° C.

TABLE 12

IPTBE SYNTHESIS
PRODUCT COMPOSITION (wt %)
METHOD 27

| Ex. | Catalyst | Temp. (°C.) | Feed Rate (cc/hr) | Sample | $C_4H_8$ | MeOH+ MeF | IPA | tBA | MTBE | IPF | IPTBE | $C_8H_{16}$ | DTBP | -METHOD 26- $H_2O$ |
|---|---|---|---|---|---|---|---|---|---|---|---|---|---|---|
| 14 | CP316-26[a] | | | FS-1 | 0.5 | 2.1 | 11.3 | 82.5 | — | — | — | — | 2.8 | 0.3 |
| | | 60 | 12 | 1 | 2.4 | 2.4 | 10.0 | 78.7 | — | 1.1 | 2.0 | — | 2.7 | 1.6 |
| | | | | 2 | 2.5 | 2.4 | 10.0 | 78.5 | | 1.2 | 2.2 | | 2.8 | 1.5 |
| | | 80 | | 3 | 8.7 | 1.1 | 9.5 | 66.9 | 4.7 | 1.0 | 4.8 | — | 2.8 | 4.8 |
| | | | | 4 | 7.9 | 1.1 | 9.6 | 67.7 | 4.5 | 1.0 | 4.8 | 0.1 | 1.8 | 4.7 |

[a]Y-Zeolite, 1/16E

What is claimed:

1. A two-step process for the generation of isopropyl t-butyl ether from a crude by-product acetone stream, containing methanol and t-butanol in an amount of 10% to 40% which comprises:
   a) Hydrogenating said crude acetone over a bulk metal, nickel-rich catalyst comprising 60%–85% nickel, 1%–30% copper and 0.1%–6% chromium, at a temperature in the range of 120°–180° C., to give an isopropanol-rich effluent;
   b) subjecting said isopropanol-rich intermediate to etherification conditions in the presence of a strong acid catalyst selected from the group consisting of:
      (1) a cationic resin;
      (2) a β-zeolite;
      (3) dealuminized Y-zeolites; and
      (4) metal modified β-zeolites at a temperature from 20° C. to 250° C. and a pressure of 0 to 5000 psig, to generate isopropyl t-butyl ether.

2. The process of claim 1 wherein the etherification catalyst is a cationic resin selected from the group consisting of a gel type resin and a macroreticular ion exchange resin.

3. The process of claim 2 wherein the cationic resin is a macroreticular ion exchange resin having a sulfonic acid (—S₃H) functionality.

4. The process of claim 3 wherein the sulfonic acid functional group is bonded directly or indirectly to an organic polymer backbone.

5. The process of claim 3 wherein the macroreticular resin is a macroporous resin with a styrene-divinylbenzene polymer backbone, a sulfonic acid functionality, and 1–20% cross-linking.

6. The process of claim 1 wherein the β-zeolite etherification catalyst has a silica:alumina molar ratio of at least 10:1.

7. The process of claim 1 wherein the β-zeolite has a silica:alumina molar ratio in the range of 10:1 to 50:1.

8. The process of claim 1 wherein the β-zeolite has a surface area, after calcination, of at least 100 m²/g.

9. The process of claim 1 wherein the β-zeolite is characterized by the following X-ray diffraction, pattern:
   11.40±0.2
   7.40±0.2
   6.70±0.2
   4.25±0.1
   3.97±0.1
   3.00±0.1
   2.20±0.1

10. The process of claim 1 wherein the β-zeolite is modified with one or more metals selected from the group consisting of Groups IB, VIB, VIIB and VIII of the Periodic Table.

11. The process of claim 10 wherein the β-zeolite is modified with one or more metals selected from the group consisting of iron, chromium, manganese, copper, nickel, palladium and platinum.

12. The process of claim 11 wherein the β-zeolite is modified with one or more metals selected from the group consisting of iron, chromium and manganese.

13. The process of claim 11 wherein the β-zeolite is modified with platinum.

14. The process of claim 11 wherein the β-zeolite is modified with palladium.

15. The process of claim 10 wherein the β-zeolite is treated with a fluoride-containing compound.

16. The process of claim 11 wherein the β-zeolite is modified with one or more metals selected from the group consisting of nickel and copper.

17. The process of claim 10 wherein the concentrations of metals deposited on said zeolite may vary from 0.01% to 10.0% for each metal.

18. The process of claim 1 wherein the β-zeolite catalyst is modified and treated in the presence of a binder selected from the group consisting of Group III oxide or a Group IV oxide.

19. The process of claim 18 wherein the Group III oxide binder is alumina.

20. The process of claim 19 wherein the alumina comprises 10% to 90% of the formed catalyst.

21. The process of claim 1 wherein the dealuminized Y-zeolite has a silica-to-alumina molar ratio of greater than 3.

22. The process of claim 21 wherein the Y-zeolite is dealuminated and has a silica-to-alumina molar ratio in the range 40 to 50 and a unit cell size in the range 24.00 to 24.50.

23. The process of claim 1 wherein the crude by-product acetone stream contains 10% to 80% acetone.

24. The process of claim 1 wherein the —isopropanol-rich intermediate is subjected to etherification conditions—in the temperature range of 200° to 100° C.

25. The process of claim 1 wherein the —isopropanol-rich intermediate is subjected to etherification conditions—in the temperature range of 40°–80° C.

26. A two-step process for the cogeneration of isopropyl t-butyl ether and methyl tertiary butyl ether from a crude acetone stream, containing methanol and t-butanol in an amount of about 10% to 40%, which comprises:
   a) Hydrogenating said crude acetone over a nickel catalyst consisting essentially of 60–85 mol % nickel, 1–30 mol % copper and 0.1–6 mol % chromium at a temperature in the range of 120° C. to 180° C. to give an isopropanol-rich effluent;

b) subjecting said isopropanol-rich intermediate to dehydration conditions in the presence of a strong acidic catalyst selected from:
(1) a cationic resin;
(2) a β-zeolite;
(3) a dealuminized Y-zeolite; and
(4) a metal-modified β-zeolite at a temperature from 20° C. to 250° C. and a pressure of 0 to 5000 psig.

27. The process of claim 1 wherein the Y-zeolite is a dealuminated Y-zeolite selected from the group consisting of:
a) ammonium exchanged Y-zeolites;
b) Y-zeolites treated with ethylenediaminetetraacetic acid;
c) Y-zeolites treated with a fluorine-containing compound selected from the group consisting of silicon tetrafluoride and ammonium fluorosilicate; and
d) Y-zeolites treated with steam alone or steam followed by acid treatment.

* * * * *